(12) United States Patent
Rao et al.

(10) Patent No.: US 10,451,624 B2
(45) Date of Patent: Oct. 22, 2019

(54) REAGENT KIT USED FOR DETECTING LIPOPROTEIN-ASSOCIATED PHOSPHOLIPASE A2, AND PREPARATION METHOD AND APPLICATION FOR REAGENT KIT

(71) Applicant: SHENZHEN NEW INDUSTRIES BIOMEDICAL ENGINEERING CO., LTD., Shenzhen (CN)

(72) Inventors: Wei Rao, Shenzhen (CN); Jinyun Yuan, Shenzhen (CN); Qin Li, Shenzhen (CN); Ke Huang, Shenzhen (CN); Kai Luo, Shenzhen (CN); Dongxia Lin, Shenzhen (CN); Tinghua Li, Shenzhen (CN)

(73) Assignee: SHENZHEN NEW INDUSTRIES BIOMEDICAL ENGINEERING CO., LTD, Shenzhen (CN)

( * ) Notice: Subject to any disclaimer, the term of this patent is extended or adjusted under 35 U.S.C. 154(b) by 285 days.

(21) Appl. No.: 15/543,817

(22) PCT Filed: Feb. 10, 2015

(86) PCT No.: PCT/CN2015/072676
§ 371 (c)(1),
(2) Date: Jul. 14, 2017

(87) PCT Pub. No.: WO2016/127319
PCT Pub. Date: Aug. 18, 2016

(65) Prior Publication Data
US 2017/0363627 A1 Dec. 21, 2017

(51) Int. Cl.
*G01N 33/53* (2006.01)
*G01N 33/573* (2006.01)
*C12Q 1/44* (2006.01)

(52) U.S. Cl.
CPC ............ *G01N 33/573* (2013.01); *C12Q 1/44* (2013.01); *C12Y 301/01004* (2013.01); *G01N 2333/918* (2013.01)

(58) Field of Classification Search
None
See application file for complete search history.

(56) References Cited

U.S. PATENT DOCUMENTS

| | | | | |
|---|---|---|---|---|
| 6,524,865 B1 * | 2/2003 | Martin | ................ | C07F 15/0053 |
| | | | | 435/18 |
| 9,000,132 B2 | 4/2015 | Miller et al. | | |
| 2004/0096925 A1 | 5/2004 | Perrier et al. | | |
| 2005/0058649 A1 * | 3/2005 | Landes | ................. | C07K 16/40 |
| | | | | 424/146.1 |
| 2005/0266570 A1 * | 12/2005 | Carey | .................... | B01L 3/508 |
| | | | | 436/43 |
| 2007/0065892 A1 * | 3/2007 | Hu | ........................... | C12N 9/20 |
| | | | | 435/15 |
| 2014/0275485 A1 * | 9/2014 | Miller | .................... | C07K 16/40 |
| | | | | 530/387.3 |
| 2016/0334404 A1 * | 11/2016 | Schaal | ..................... | C12N 9/96 |
| 2017/0184615 A1 | 6/2017 | Rao et al. | | |

FOREIGN PATENT DOCUMENTS

| | | |
|---|---|---|
| CN | 1888901 A | 1/2007 |
| CN | 101441219 A | 5/2009 |
| CN | 103645326 A | 3/2014 |
| CN | 103698535 A | 4/2014 |
| CN | 103792353 A | 5/2014 |
| CN | 104007260 A | 8/2014 |
| CN | 104133062 A | 11/2014 |
| CN | 104231052 A | 12/2014 |
| EP | 2280282 A1 | 2/2011 |
| WO | 2016/127320 A1 | 8/2016 |

OTHER PUBLICATIONS

Albert et al., The effect of statin therapy on lipoprotein associated phospholipase A2 levels, Atheroscerosis, 182, 2005, pp. 193-198. (Year: 2005).*
International Search Report and English Translation thereof for International Application No. PCT/CN2015/072676, dated Nov. 23, 2015 (8 pages).
Rao et al., U.S. Appl. No. 15/507,630, filed Feb. 10, 2015.
Rao et al., U.S. Appl. No. 15/540,839, filed Jan. 20, 2017.
Extended European Search Report for Application No. 15881481.4, dated Jun. 19, 2018, (7 pages).

* cited by examiner

*Primary Examiner* — Gary Counts
(74) *Attorney, Agent, or Firm* — Kagan Binder, PLLC

(57) ABSTRACT

A reagent kit used for detecting lipoprotein-associated phospholipase A2, and a preparation method for the reagent kit. The reagent kit comprises one or a plurality of first anti-lipoprotein-associated phospholipase A2 antibodies used for binding lipoprotein-associated phospholipase A2 to be measured, and one or a plurality of second anti-lipoprotein-associated phospholipase A2 antibodies marked with a trace marker and binding with the lipoprotein-associated phospholipase A2 to be measured at another site, different from the binding site of the lipoprotein-associated phospholipase A2 to be measured and the first anti-lipoprotein-associated phospholipase A2 antibodies. The reagent kit also comprises a displacing agent, so as to further increase the detection accuracy of the reagent kit. A method using the reagent kit for the detection of lipoprotein-associated phospholipase A2 may take serum as a detection sample, has high repeatability and high accuracy, and measures the concentration of lipoprotein-associated phospholipase A2 in the sample in a highly sensitive manner.

20 Claims, 3 Drawing Sheets

REAGENT KIT USED FOR DETECTING LIPOPROTEIN-ASSOCIATED PHOSPHOLIPASE A2, AND PREPARATION METHOD AND APPLICATION FOR REAGENT KIT

CROSS-REFERENCE TO RELATED APPLICATIONS

The application is a U.S. national stage application under 35 U.S.C. § 371 of International Application No. PCT/CN2015/072676 filed Feb. 10, 2015.

TECHNICAL FIELD

The present disclosure relates to the field of detection of biochemical substances. More particularly, it relates to a kit for detecting lipoprotein-associated phospholipase A2 and a method for producing the same, as well as a method for detecting lipoprotein-associated phospholipase A2.

BACKGROUND

Lp-PLA2, also known as platelet activating factor acetylhydrolase (PAF-AH), is encoded by the PLA2G7 gene and is a member of the class PLA2 of the phospholipase family. It is a serine-dependent phospholipase which has a catalytic activity with no need for $Ca^{2+}$. Human plasma Lp-PLA2 has a molecular weight of 45 kDa and is mainly produced by secretion of macrophages, monocytes, T lymphocytes, mast cells, hepatocytes, and the like, with regulation by inflammatory mediators. For example, its secretion can be inhibited by gamma interferon and lipopolysaccharide but enhanced by platelet activating factor. The main roles of Lp-PLA2 include producing dodecanoic acid inflammatory substances, participating in phospholipid reconstitution and stable equilibrium of biological membrane, lipoprotein metabolism, cell signaling, and host reaction, and facilitating autologous disappearing of necrotic tissue of the body.

Recent studies have shown that Lp-PLA2 can promote the formation of atherosclerotic (AS) plaques and bind to low density lipoprotein (LDL) in the circulation. The current study suggests that coronary heart disease (CHD) is a chronic inflammatory disease, with inflammation involved in various stages of CHD pathogenesis. Lp-PLA2 is secreted by inflammatory cells in the atherosclerotic plaques and is significantly increased in severe atherosclerotic plaques. Therefore, it can be used as a marker for predicting future cardiovascular events of CHD. Other studies have found that Lp-PLA2 is correlated with a risk of congestive heart failure (CHF). The onset of cerebral infarction is closely related to the instability of the AS plaque, while instable plaques, in turn, are prone to embolization or thrombosis, leading to infarction. Lp-PLA2 may be an independent predictor of ischemic stroke, and determination of Lp-PLA2 level may provide predictive information in addition to conventional risk factor assessment, providing insights for guiding the prevention strategy. Studies have found that low-level inflammatory response plays an important role when metabolic syndrome (MS) occurs, wherein the MS health response becomes more obvious with increased activity of Lp-PLA2.

At present, methods for determination of Lp-PLA2 available on the market mainly involve spectrophotometry, latex-enhanced turbidimetry, radioactive immunoassay (RIA), and enzyme-linked immunosorbent assay (ELISA).

Among them, there are currently two types of spectrophotometrical methods for detecting Lp-PLA2. One method uses PAF thioesters as the substrate. Its mechanism involves enzymatic hydrolysis of the thioester group in the sn-2 position on the backbone of the PAF thioester analogue, releasing free thiol, followed by addition of 5'S-disulfide (dinitrobenzoic acid) of the thiol which can be detected, and detection of variation in absorbance at 405 nm. This type of substrates includes 1-thiodecanoyl-2-decanoyl-PC, 1-hexadecanoyl-2-thiohexadecanoyl-PC, and the like. The other method uses PAF analogues with a 4-nitrophenol group. This type of substrate has similar structure with the PAF thioester, except that the thioester group in the sn-2 position is displaced by the 4-nitrophenol group. Its mechanism involves enzymatic hydrolysis of the substrate, releasing the substance with 4-nitrophenol group which has instable properties and immediately decomposes into 4-nitrophenol, and detection of variation in absorbance at 405 nm due to this change, thereby determining the enzyme activity.

In latex-enhanced turbidimetry, Lp-PLA2 in a sample undergoes an antigen-antibody reaction with sensitized latex particles of mouse anti-human Lp-PLA2 antibody in the reagent in a phosphate buffer system, causing agglutination under the action of polyethylene glycol as an accelerator to produce an increased turbidity, and variation in absorbance of the reaction solution is detected at 546 nm wavelength, which is proportional to the Lp-PLA2 content in the sample.

Radioimmunoassay involves a procedure in accordance with the principle of competition mechanism, wherein the binding amount of 1251-Lp-PLA2 with antibody is a function of the Lp-PLA2 content in the standard or sample. The Lp-PLA2 concentration in the sample was determined by separating the binding fraction (B) from the free fraction (F) using an immune separation agent (PR), determining the radioactive intensity of the binding fraction, and processing the data.

Enzyme-linked immunosorbent assay (ELISA) uses a double antibody sandwich method to determine the level of human Lp-PLA2 in whole blood samples. Purified human Lp-PLA2 antibodies are used to coat a microplate to prepare solid phase antibody. Lp-PLA2 is added to the wells coated on the monoclonal antibody and binds with the anti-Lp-PLA2 antibody labeled with horseradish peroxidase (HRP) to form an antibody-antigen-enzyme-labeled antibody complex. TMB (3, 3", 5, 5"-tetramethylbenzidine) was added as a substrate after thorough washing for coloration. TMB is converted to blue under the catalysis of HRP enzyme and to a final yellow color under the action of acid. The color tone is positively correlated with the Lp-PLA2 content in the sample. The absorbance (OD) is measured at 450 nm using a microplate reader. The content of human Lp-PLA2 in the sample is calculated using a standard curve. Enzyme-linked immunosorbent assay (ELISA) is a commonly used method for determination of Lp-PLA2. However, there is plenty of interferential components in the whole blood samples for Lp-PLA2 measurement, which affects the accuracy of measurement. Besides, the enzyme immunoluminescence antibody coating for selection is limited to a single form and the binding with Lp-PLA2 is not thorough enough, resulting in low detection sensitivity. Relatively large numbers of uncertain factors in the microplate has caused poor repeatability of the test. In addition, enzyme-linked immunoassay is restricted by its degree of automation, rendering a relatively long reaction time.

SUMMARY OF THE INVENTION

As one object of the present disclosure, a kit is provided for detecting Lp-PLA2. Using this kit, the concentration of Lp-PLA2 can be detected with high sensitivity, high repeatability, and high accuracy with a double antibody sandwich method. Particularly, with the addition of a displacer in the kit, the precision of Lp-PLA2 detection can be further improved.

The present disclosure also provides a method for preparing a chemiluminescence immunoassay kit for detecting Lp-PLA2.

Further, the present disclosure also provides applications of the Lp-PLA2 chemiluminescence immunoassay kit according to the present disclosure, in particular the application of the kit in performing a fully-automated chemiluminescence method for Lp-PLA2 detection to shorten operating time, reduce operation errors, and improve detection sensitivity with the specificity of chemical trace marker.

According to the present disclosure, a kit for detecting Lp-PLA2 is provided, comprising one or more first anti-Lp-PLA2 antibodies coated on magnetic sphere for binding with Lp-PLA2 to be detected, and one or more second anti-Lp-PLA2 antibodies labeled with a trace marker for binding with Lp-PLA2 to be detected at other binding sites different from the binding sites on Lp-PLA2 for the first anti-Lp-PLA2 antibodies. That is, the difference between the first anti-Lp-PLA2 antibody and the second anti-Lp-PLA2 antibody lies in their different binding sites on Lp-PLA2 to be detected. Thus, in an equivalent embodiment of the present disclosure, the kit comprises one or more second anti-Lp-PLA2 antibodies coated on magnetic sphere for binding with Lp-PLA2 to be detected, and one or more first anti-Lp-PLA2 antibodies labeled with a trace marker for binding with Lp-PLA2 to be detected at other binding sites different from the binding sites on Lp-PLA2 for the first anti-Lp-PLA2 antibodies.

According to the present disclosure, the first anti-Lp-PLA2 antibody and the second anti-Lp-PLA2 antibody may each independently be an anti-Lp-PLA2 monoclonal antibody and/or an anti-Lp-PLA2 polyclonal antibody.

According to the present disclosure, the trace marker may be selected from trace markers commonly used in the art for labeling antigens or antibodies, such as adamantane, luminol and its derivatives, isluminol and its derivatives, acridinium esters, alkaline phosphatase or horseradish peroxidase, and particularly preferably N-(4-aminobutyl)-N-ethylisoluminol (ABEI).

Magnetic sphere suitable for use in the present disclosure are also known as magnetic beads and may be magnetic microspheres commonly used in the art. It is preferable that the magnetic sphere used in the present disclosure are microscale solid-phase microspheres with superparamagnetism and extremely large capacity of protein adsorption formed by combining nanoscale $Fe_2O_3$ or $Fe_3O_4$ magnetic particles and an organic polymeric materials. Such magnetic sphere can be quickly magnetized in an applied magnetic field while having a remanence of zero after removal of the magnetic field. There is no particular limitation on the types of the organic polymeric material, which may be selected as necessary.

The magnetic microspheres used in the present disclosure should have a diameter of 0.1 to 5 microns, and the magnetic microspheres may be surface modified to carry a variety of reactive functional groups including, but not limited to, —OH, —COOH, —NH$_2$.

In a specific embodiment, the magnetic sphere is a complex of $Fe_2O_3$ or $Fe_3O_4$ magnetic particles and an organic polymeric material and has a particle size of 0.1 to 5 microns; and, the magnetic sphere are optionally modified by surface modification to carry one or more active functional groups.

According to the present disclosure, the concentrations of the first anti-Lp-PLA2 antibody and the second anti-Lp-PLA2 antibody in the kit are 10 to 200 μg/ml, respectively, the concentration of the trace marker is 0.1 to 1 mg/ml, and the concentration of the magnetic sphere is 0.1 to 5 mg/ml. The concentration for each component above is based on the amount of each independent component containing such component.

According to the present disclosure, the kit further comprises a low-point calibrator and a high-point calibrator of Lp-PLA2 and optionally a buffer. The low-point calibrator and high-point calibrator herein is referred to relative to each other, wherein the "low-point calibrator" refers to a calibrator made by diluting Lp-PLA2 to a concentration of 10 to 30 ng/ml using a 50% bovine serum product, and the "high-point calibrator" refers to a calibrator made by diluting Lp-PLA2 to a concentration of 500 to 700 ng/ml using a 50% bovine serum product. The low-point calibrator and high-point calibrator each optionally contains bovine serum albumin (BSA) and/or a preservative. The BSA concentration is preferably 0.01 to 5 g/ml.

According to the present disclosure, the trace marker directly or indirectly labels the second anti-Lp-PLA2 antibody. Indirect labeling forms include, but are not limited to, indirect labeling via a fluorescein isothiocyanate (FITC) and anti-FITC antibody system or a streptavidin (SA) and biotin system. Direct labeling refers to labeling by directly linking ABEI to an anti-Lp-PLA2 antibody. Indirect labeling refers to labeling an anti-Lp-PLA2 antibody with ABEI via an intermediate medium linking system including, but not limited to, a FITC and anti-FITC antibody system or a streptavidin and biotin system. The present inventors have found that indirect marking advantageously weakens the spatial effect and facilitates the amplification of the signal, increasing detection sensitivity. The anti-FITC antibody is preferably a goat anti-FITC polyclonal antibody.

According to the present disclosure, the first anti-Lp-PLA2 antibodies are directly or indirectly coated on magnetic sphere. Indirect coating forms of the magnetic sphere include, but are not limited to, indirect coating by a FITC and anti-FITC antibody system or a streptavidin and biotin system. Direct coating refers to coating the magnetic sphere directly using anti-Lp-PLA2 antibodies; and indirect coating refers to coating the magnetic sphere using the anti-Lp-PLA2 antibodies via an intermediate medium linking system including, but not limited to, a FITC and anti-FITC antibody system or a streptavidin and biotin system. One advantage of indirect coating lies in that it weakens the spatial effect and facilitates the amplification of the signal, increasing detection sensitivity.

In some embodiments according to the present disclosure, the first anti-Lp-PLA2 antibodies are capable of binding to the sites 220 to 441 on Lp-PLA2, and the second anti-Lp-PLA2 antibodies are capable of binding to the sites 1 to 200 on Lp-PLA2. In a further embodiment, the first anti-Lp-PLA2 antibodies are coated on magnetic sphere, and the second anti-Lp-PLA2 antibodies are labeled with a trace marker. In these embodiments, the first anti-Lp-PLA2 antibodies are directly or indirectly coated on magnetic sphere, and the indirect coating forms of magnetic sphere comprise indirect coating via a FITC and anti-FITC antibody system or a streptavidin and biotin system. The trace marker directly or indirectly labels the second anti-Lp-PLA2 antibody, and the indirect labeling forms comprise indirect labeling via a FITC and anti-FITC antibody system or a streptavidin and biotin system.

According to some embodiments of the present disclosure, the kit comprises any one of the components selected from M1 to M3 and any one of the components selected from N1 to N3, wherein M1 is a solution of the first anti-Lp-PLA2 antibody directly coated on magnetic sphere; M2 is a streptavidin solution directly coated on magnetic sphere and a biotinylated solution of the second anti-Lp-PLA2 antibody; M3 is an solution of anti-FITC antibody directly coated on magnetic sphere and a solution of the second anti-Lp-PLA2 antibody labeled with FITC; N1 is a solution of the first anti-Lp-PLA2 antibody directly labeled with a trace marker; N2 is a streptavidin solution directly labeled with a trace marker and a biotinylated solution of the first anti-Lp-PLA2 antibody; N3 is a solution of anti-FITC antibody directly labeled with a trace marker and a solution of the first anti-Lp-PLA2 antibody solution labeled with FITC; and, each solution of the components M1 to M3 and the components N1 to N3 optionally comprises BSA and/or a preservative. The BSA concentration is preferably 0.01 to 5 g/ml.

In a specific embodiment of the present disclosure, the kit comprises:

a1) a suspension of magnetic sphere coated with the first anti-Lp-PLA2 antibody, in which the concentration of the first anti-Lp-PLA2 antibody is 10 to 200 µg/ml and the concentration of magnetic sphere is 0.1 to 5 mg/ml;

b1) a solution of the second anti-Lp-PLA2 antibody labeled with ABEI, in which the concentration of the second anti-Lp-PLA2 antibody is 10 to 200 µg/ml and the ABEI concentration is 0.1 to 1 mg/ml;

c1) a low-point calibrator containing Lp-PLA2 at a concentration of 10 to 30 ng/ml;

d1) a high-point calibrator containing Lp-PLA2 at a concentration of 500 to 700 ng/ml;

Each of the components contains BSA and a preservative, the BSA concentration being 0.01 to 5 g/ml.

In a specific embodiment of the present disclosure, the kit comprises:

a2) a solution of magnetic sphere coated with streptavidin, in which the concentration of streptavidin is 10 to 200 µg/ml and the concentration of magnetic sphere is 0.1 to 5 mg/ml;

b2) a solution of the second anti-Lp-PLA2 antibody labeled with ABEI, in which the concentration of the second anti-Lp-PLA2 antibody is 10 to 200 µg/ml and the ABEI concentration is 0.1 to 1 mg/ml;

c2) a biotinylated solution of the first anti-Lp-PLA2 antibody, in which the concentration of the first anti-Lp-PLA2 antibody is 10 to 200 µg/ml and the concentration of biotin is 0.1 to 1 mg/ml;

d2) a low-point calibrator containing Lp-PLA2 at a concentration of 10 to 30 ng/ml;

e2) a high-point calibrator containing Lp-PLA2 at a concentration of 500 to 700 ng/ml;

Each of the components contains BSA and a preservative, the BSA concentration being 0.01 to 5 g/ml.

In a specific embodiment of the present disclosure, the kit comprises:

a3) a solution of magnetic sphere coated with anti-FITC antibodies, in which the concentration of anti-FITC antibodies is 10 to 200 µg/ml and the concentration of magnetic sphere is 0.1 to 5 mg/ml;

b3) a solution of the second anti-Lp-PLA2 antibody labeled with ABEI, in which the concentration of the second anti-Lp-PLA2 antibody is 10 to 200 µg/ml and the ABEI concentration is 0.1 to 1 mg/ml;

c3) a solution of the first anti-Lp-PLA2 antibody labeled with FITC, in which the concentration of the first anti-Lp-PLA2 antibody is 10 to 200 µg/ml and the concentration of FITC is 0.1 to 1 mg/ml;

d3) a low-point calibrator containing Lp-PLA2 at a concentration of 10 to 30 ng/ml;

e3) a high-point calibrator containing Lp-PLA2 at a concentration of 500 to 700 ng/ml;

Each of the components contains BSA and a preservative, the BSA concentration being 0.01 to 5 g/ml.

In a specific embodiment of the present disclosure, the kit comprises:

a4) a solution of magnetic sphere coated with the first anti-Lp-PLA2 antibodies, in which the concentration of the first anti-Lp-PLA2 antibodies is 10 to 200 µg/ml and the concentration of magnetic sphere is 0.1 to 5 mg/ml;

b4) a biotinylated solution of the second anti-Lp-PLA2 antibody, in which the concentration of the second anti-Lp-PLA2 antibody is 10 to 200 µg/ml and the biotin concentration is 0.1 to 1 mg/ml;

c4) a solution of streptavitin labeled with ABEI, in which the concentration of streptavidin is 10 to 200 µg/ml and the concentration of ABEI is 0.1 to 1 mg/ml;

d4) a low-point calibrator containing Lp-PLA2 at a concentration of 10 to 30 ng/ml;

e4) a high-point calibrator containing Lp-PLA2 at a concentration of 500 to 700 ng/ml;

Each of the components contains BSA and a preservative, the BSA concentration being 0.01 to 5 g/ml.

The present disclosure also provides a displacer comprising water as a solvent (preferably purified water) and the following components:

at least one selected from the group consisting of 3-[3-(cholamidopropyl) dimethylammonio] propanesulfonate, 8-anilino-1-naphthalenesulfonic acid, sodium deoxycholate, barbiturate, and acetic acid;

newborn bovine serum;

goat serum and/or horse serum;

dithiothreitol;

tris (hydroxymethyl) aminomethane;

hydrated 2-morpholinoethanesulfonic acid;

casein; and disodium ethylenediaminetetraacetate.

In a preferred embodiment of the present disclosure, the displacer comprises the following components relative to the total amount of the solvent:

at least one selected from the group consisting of 0.1 to 5 wt % of 3-[3-(cholamidopropyl) dimethylammonio] propanesulfonate (CHAPS), 0.1 to 2 wt % of 8-anilino-1-naphthalenesulfonic acid (ANS), 0.1 to 2 wt % of sodium deoxycholate (SDC), 0.1 to 2 wt % of barbiturate, and 0.1 to 2 vol % of acetic acid;

1 to 50 vol % of newborn bovine serum;

0.1 to 10 vol % of goat serum and/or 0.1 to 10 vol % of horse serum;

0.1 to 10 wt % of dithiothreitol (DDT);

0.1 to 10 wt % of tris (hydroxymethyl) aminomethane (Tris);

0.1 to 10 wt % of monohydrate 2-morpholinoethanesulfonic acid (MES);

0.01 to 1 wt % of casein; and 0.01 to 1 wt % of disodium ethylenediaminetetraacetate (EDTA-2Na).

The displacer may further comprise 0.1 to 10 vol % of ethylene glycol and/or 0.1-10 vol % of glycerol.

The displacer may further comprise an appropriate amount of preservative.

The preservatives suitable for use in the present disclosure may be any one or a mixture of at least two or more selected from preservatives commonly used in the art, such as potassium sorbate, sodium benzoate, sodium azide, sodium nitrite, the Proclin series, or the like.

In a preferred embodiment of the present disclosure, the kit provided herein further comprises a displacer as described above. Since Lp-PLA2 is present in the human body primarily as a complex with the lipoprotein particles, the Lp-PLA2 antigen can be displaced from the complex with lipoprotein particles by the above-mentioned displacer so as to better react with an antibody. Therefore, the accuracy and sensitivity of the reagent can be remarkably improved by utilizing the function and characteristics of the displacer as described above.

The present disclosure provides a method for preparing a kit as described above, comprising: directly or indirectly coating a first anti-Lp-PLA2 antibody on magnetic sphere, and directly or indirectly labeling a second anti-Lp-PLA2 antibody with a trace marker.

In the method according to the present disclosure, the indirect labeling comprises labeling the second anti-Lp-PLA2 antibody with a trace marker via a FITC and anti-FITC antibody system or a streptavidin and biotin system.

In the method according to the present disclosure, the indirect coating comprises coating the first anti-Lp-PLA2 antibody indirectly through a FITC and anti-FITC antibody system or a streptavidin and biotin system.

The method for preparing a kit according to the present disclosure comprises directly or indirectly coating the first anti-Lp-PLA2 antibodies on magnetic sphere, and directly or indirectly labeling the second anti-Lp-PLA2 antibodies with a trace marker; wherein, the first anti-Lp-PLA2 antibodies bind to the sites 220-441 on the lipoprotein-associated phospholipase A2 and the second anti-Lp-PLA2 antibodies bind to the sites 1 to 200 on the lipoprotein-associated phospholipase A2. In these embodiments, the forms of indirect labeling comprise indirect labeling via a fluorescein isothiocyanate and anti-fluorescein isothiocyanate antibody system or a streptavidin and biotin system; and, the indirect coating forms of the magnetic sphere comprise indirect coating via a fluorescein isothiocyanate and anti-fluorescein isothiocyanate antibody system or a streptavidin and biotin system.

The method for preparing a kit according to the present disclosure may further comprise preparing a low-point calibrator and a high-point calibrator, and it may further comprise assembling the kit.

According to the present disclosure, there is also provided a method for detecting Lp-PLA2, which comprises detecting Lp-PLA2 concentration in a subject sample by chemiluminescence immunoassay using a kit as described above.

In one embodiment, the method comprises detecting the concentration of Lp-PLA2 in a subject sample by chemiluminescent immunoassay using a kit as described above. Specifically, the first anti-Lp-PLA2 antibodies coated on the magnetic sphere in the kit and the second anti-Lp-PLA2 antibodies labeled with a trace marker are allowed to form a double antibody sandwich mode of the first anti-PLA2 antibody/Lp-PLA2/second anti-Lp-PLA2 antibody, with Lp-PLA2 in the subject sample, and luminescent substrate is added for determination of Lp-PLA2 concentration by chemiluminescence immunoassay.

In one embodiment, the method for detecting Lp-PLA2 concentration comprises detecting Lp-PLA2 concentration by a chemiluminescence immunoassay analyser using a kit as described above. In a preferred embodiment of the present disclosure, the method is performed in full automation. According to the present disclosure, the chemiluminescence immunoassay analyser is preferably a Maglumi series chemiluminescence immunoassay analyzer (manufactured by Shenzhen New Industries Biomedical Engineering Co., Ltd.).

Detection of Lp-PLA2 by the kit provided herein can utilize a serum sample as a subject sample, eliminating the interference factors in the plasma and sparing the time for pretreatment of a whole blood sample. The kit provided herein utilizes a variety of antibody labeling forms. In addition, the use of a displacer can specifically displace Lp-PLA2 to ensure effective and accurate binding of antibodies and antigens and improve detection accuracy and sensitivity.

The method for detecting Lp-PLA2 provided herein adopts an one-step process, that is, adding the components of the kit and the antigens to be detected into a reaction cup in one step for a mixed reaction to form a double antibody sandwich mode, which reduces operation steps and reaction time; it is also possible to utilize a machine to add samples to effectively reduce human errors and improve repeatability.

DETAILED DESCRIPTION OF THE INVENTION

Figure 1:
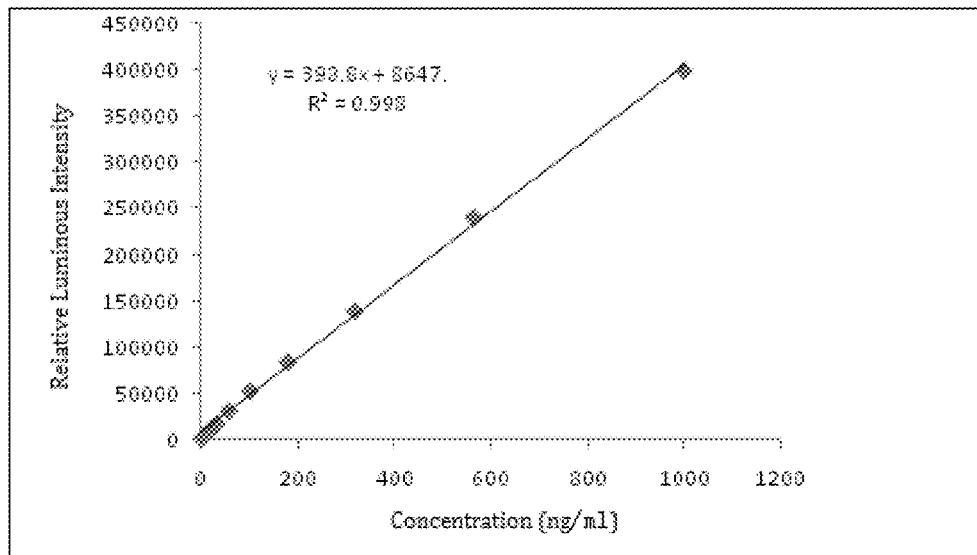
FIG. 1 show a linear fit plot of the Lp-PLA2 concentration and the relative luminous intensity according to Example 1.

The present disclosure will now be further described by way of specific embodiments and specific examples, and it is to be understood that the scope of the disclosure is not limited thereto.

The method for preparing the components of the kit is as follows:

Preparation Example 1: Preparation of a Suspension of Magnetic Sphere Coated with Anti-Lp-PLA2 Monoclonal or Polyclonal Antibodies The immunomagnetic sphere used in this preparation procedure was a suspension of nano-magnetic microspheres at a concentration of 100 mg/ml with hydroxyl group of 95 mg KOH/g, manufactured by Merck Co., Ltd.

(1) Preparation of Buffer:

2.55 g sodium acetate trihydrate was weighed, dissolved in 4500 ml of purified water, added with 14 ml acetic acid, and well mixed to produce an acetic acid buffer, pH 3.6.

(2) Linking of the Magnetic Microspheres (CMC Method for Linking Magnetic Microspheres):

The magnetic microspheres were suspended in the acetic acid buffer (pH 3.6) above of 5× coating volume to give a magnetic sphere concentration of 20 mg/ml, and 1-cyclohexyl-2-morpholinoethyl-carbodiimide metho-p-toluenesulfonate (CMC) was added to a concentration of 10 mg/ml. Purified anti-Lp-PLA2 monoclonal or polyclonal antibodies were added by a weight ratio of the resultant solution to the anti-Lp-PLA2 monoclonal or polyclonal antibodies at 1 mg: 12 µg, and underwent reaction in a constant-temperature shaking bath incubator at 37° C. for 24 hours.

(3) Cleaning of Magnetic Microspheres:

Preparation of cleaning solution for magnetic sphere: 500 ml PBS buffer (pH 7.4) was prepared with 0.1 mol/l PBS buffer and purified water at a volumetric ratio of 1:9, into which 2.5 g BSA was added, well mixed, and dissolved to prepare the cleaning solution for magnetic sphere.

Cleaning: the magnetic sphere after the warm bath in step (2) were poured into a beaker, placed on magnet for precipitation, had the supernatant removed, washed under stirring with 5× volume of the cleaning solution for magnetic sphere, placed on magnet, and had the cleared supernatant removed. The cleaning procedure was repeated for four times.

(4) Suspension of the Magnetic Sphere:

The magnetic sphere cleaned in step (3) were added to a mixed solution (primary composition of the mixed solution: 0.2 g/ml $KH_2PO_4$, 2.9 g/ml $NaHPO_4$, 8 g/ml NaCl, 2 g/ml $NaN_3$, 5 g/ml BSA, 2 ml/ml Twain T-20, balanced with purified water) of 1× coating volume, to obtain a suspension of magnetic sphere of 1× coating volume with a suspension concentration of 20 mg/ml, i.e., the suspension of magnetic sphere coated with the anti-Lp-PLA2 monoclonal or polyclonal antibodies.

Preparation Example 2: Preparation of a Suspension of Magnetic Sphere Coated with Streptavidin The immunomagnetic sphere used in this preparation procedure was a suspension of nano-magnetic microspheres at a concentration of 100 mg/ml with hydroxyl group of 95 mg KOH/g, manufactured by Merck Co., Ltd.

(1) Preparation of Buffer:

2.55 g sodium acetate trihydrate was weighed, dissolved in 4500 ml of purified water, added with 14 ml acetic acid, and well mixed to produce an acetic acid buffer, pH 3.6.

(2) Linking of the Magnetic Microspheres (CMC Method for Linking Magnetic Microspheres):

The magnetic microspheres were suspended in the acetic acid buffer (pH 3.6) above of 5× coating volume to give a magnetic sphere concentration of 20 mg/ml, and CMC (1-cyclohexyl-2-morpholinoethyl-carbodiimide metho-p-toluenesulfonate) was added to a concentration of 10 mg/ml. Streptavidin was added by a weight ratio of the resultant solution to streptavidin at 1 mg: 12 µg, and underwent reaction in a constant-temperature shaking bath incubator at 37° C. for 24 hours.

(3) Cleaning of Magnetic Microspheres:

Preparation of cleaning solution for magnetic sphere: 500 ml PBS buffer (pH 7.4) was prepared with 0.1 mol/l PBS buffer and purified water at a volumetric ratio of 1:9, into which 2.5 g BSA was added, well mixed, and dissolved to prepare the cleaning solution for magnetic sphere.

Cleaning: the magnetic sphere after the warm bath in step (2) were poured into a beaker, placed on magnet for precipitation, had the supernatant removed, washed under stirring with 5× volume of the cleaning solution for magnetic sphere, placed on magnet, and had the cleared supernatant removed. The cleaning procedure was repeated for four times.

(4) Suspension of the Magnetic Sphere:

The magnetic sphere cleaned in step (3) were added to a mixed solution (primary composition of the mixed solution: 0.2 g/ml $KH_2PO_4$, 2.9 g/ml $NaHPO_4$, 8 g/ml NaCl, 2 g/ml $NaN_3$, 5 g/ml BSA, 2 ml/ml Twain T-20, balanced with purified water) of 1× coating volume, to obtain a suspension of magnetic sphere of 1× coating volume with a suspension concentration of 20 mg/ml, i.e., the suspension of magnetic sphere coated with streptavitin.

Preparation Example 3: Preparation of a Suspension of Magnetic Sphere Coated with Anti-FITC Monoclonal or Polyclonal Antibodies The immunomagnetic sphere used in this preparation procedure was a suspension of nano-magnetic microspheres at a concentration of 100 mg/ml with hydroxyl group of 95 mg KOH/g, manufactured by Merck Co., Ltd.

(1) Preparation of Buffer:

2.55 g sodium acetate trihydrate was weighed, dissolved in 4500 ml of purified water, added with 14 ml acetic acid, and well mixed to produce an acetic acid buffer, pH 3.6.

(2) Linking of the Magnetic Microspheres (CMC Method for Linking Magnetic Microspheres):

The magnetic microspheres were suspended in the acetic acid buffer (pH 3.6) above of 5× coating volume to give a magnetic sphere concentration of 20 mg/ml, and CMC (1-cyclohexyl-2-morpholinoethyl-carbodiimide metho-p-toluenesulfonate) was added to a concentration of 10 mg/ml. Anti-FITC monoclonal or polyclonal antibodies were added by a weight ratio of the resultant solution to the anti-FITC monoclonal or polyclonal antibodies at 1 mg: 12 µg, and underwent reaction in a constant-temperature shaking bath incubator at 37° C. for 24 hours.

(3) Cleaning of Magnetic Microspheres:

Preparation of cleaning solution for magnetic sphere: 500 ml PBS buffer (pH 7.4) was prepared with 0.1 mol/l PBS buffer and purified water at a volumetric ratio of 1:9, into which 2.5 g BSA was added, well mixed, and dissolved to prepare the cleaning solution for magnetic sphere.

Cleaning: the magnetic sphere after the warm bath in step (2) were poured into a beaker, placed on magnet for precipitation, had the supernatant removed, washed under stirring with 5× volume of the cleaning solution for magnetic sphere, placed on magnet, and had the cleared supernatant removed. The cleaning procedure was repeated for four times.

(4) Suspension of the Magnetic Sphere:

The magnetic sphere cleaned in step (3) were added to a mixed solution (primary composition of the mixed solution: 0.2 g/ml $KH_2PO_4$, 2.9 g/ml $NaHPO_4$, 8 g/ml NaCl, 2 g/ml $NaN_3$, 5 g/ml BSA, 2 ml/ml Twain T-20, balanced with purified water) of 1× coating volume, to obtain a suspension of magnetic sphere of 1× coating volume with a suspension concentration of 20 mg/ml, i.e., the suspension of magnetic sphere coated with the anti-FITC monoclonal or polyclonal antibodies.

Preparation Example 4: Preparation of a Solution of ABEI-Labeled Anti-Lp-PLA2 Monoclonal or Polyclonal Antibodies (1) Preparation of pH 9.5 dialysis solution: in a 5000 ml beaker, 14.31 g of $Na_2CO_3$ and 26.46 g of $NaHCO_3$ was added, and filled up to 4500 ml with water. The dialysate prepared was placed on a magnetic stirrer for later use.

(2) A dialysis bag with an interception capacity of 14000 was chosen, a portion of which with appropriate size was prepared for later use. 1 mg of anti-Lp-PLA2 monoclonal or polyclonal antibodies was dissolved and adjusted to 1 ml with the dialysis solution prepared above, and placed into the dialysis bag. Dialysis was performed under stirring for 2 hours, and 300 μg of ABEI-hemisuccinimide-N-hydroxysuccinimide was added to the dialyzed solution for reaction at 37° C. for 2 hours to produce the solution of ABEI-labeled anti-Lp-PLA2 antibodies.

(3) Purification of the solution of ABEI-labeled anti-Lp-PLA2 antibodies obtained in the above reaction was performed on a G-25 gel column.

(4) An equal volume of 5 g/ml BSA protective solution was added to the purified solution of ABEI-labeled anti-Lp-PLA2 antibodies to obtain the final solution.

Preparation Example 5: Preparation of a Solution of Biotin-Labeled Anti-Lp-PLA2 Monoclonal or Polyclonal Antibodies (1) Preparation of pH 9.5 dialysis solution: in a 5000 ml beaker, 14.31 g of $Na_2CO_3$ and 26.46 g of $NaHCO_3$ was added, and filled up to 4500 ml with water. The dialysate prepared was placed on a magnetic stirrer for later use.

(2) A dialysis bag with an interception capacity of 14000 was chosen, a portion of which with appropriate size was prepared for later use. 1 mg of anti-Lp-PLA2 monoclonal or polyclonal antibodies was dissolved and adjusted to 1 ml with the dialysis solution prepared above, and placed into the dialysis bag. Dialysis was performed under stirring for 2 hours, and 300 μg of biotin was added to the dialyzed solution for reaction at 37° C. for 2 hours to produce the solution of biotinylated anti-Lp-PLA2 antibodies.

(3) Purification of the biotinylated anti-Lp-PLA2 antibody solution obtained in the above reaction was performed on a G-25 gel column.

(4) An equal volume of 5 g/ml BSA protective solution was added to the purified biotinylated anti-Lp-PLA2 antibody solution to obtain the final solution.

Preparation Example 6: Preparation of a Solution of FITC-Labeled Anti-Lp-PLA2 Monoclonal or Polyclonal (1) Preparation of pH 9.5 dialysis solution: in a 5000 ml beaker, 14.31 g of $Na_2CO_3$ and 26.46 g of $NaHCO_3$ was added, and filled up to 4500 ml with water. The dialysate prepared was placed on a magnetic stirrer for later use.

(2) A dialysis bag with an interception capacity of 14000 was chosen, a portion of which with appropriate size was prepared for later use. 1 mg of anti-Lp-PLA2 monoclonal or polyclonal antibodies was dissolved and adjusted to 1 ml with the dialysis solution prepared above, and placed into the dialysis bag. Dialysis was performed under stirring for 2 hours, and 100 μg of FITC was added to the dialyzed solution for reaction at 37° C. for 2 hours to produce the solution of FITC-labeled anti-Lp-PLA2 monoclonal or polyclonal antibodies.

(3) Purifying of the solution of FITC-labeled anti-Lp-PLA2 monoclonal or polyclonal antibodies obtained in the above reaction was performed on a G-25 gel column.

(4) An equal volume of 5 g/ml BSA protective solution was added to the purified solution of FITC-labeled anti-Lp-PLA2 monoclonal or polyclonal antibodies to obtain the final solution.

Preparation Example 7: Preparation of a Solution of Streptavidin-Labeled Anti-Lp-PLA2 Monoclonal or Polyclonal Antibodies (1) Preparation of pH 9.5 dialysis solution: in a 5000 ml beaker, 14.31 g of $Na_2CO_3$ and 26.46 g of $NaHCO_3$ was added, and filled up to 4500 ml with water. The dialysate prepared was placed on a magnetic stirrer for later use.

(2) A dialysis bag with an interception capacity of 14000 was chosen, a portion of which with appropriate size was prepared for later use. 1 mg of anti-Lp-PLA2 monoclonal or polyclonal antibodies was dissolved and adjusted to 1 ml with the dialysis solution prepared above, and placed into the dialysis bag. Dialysis was performed under stirring for 2 hours, and 50 μg of streptavidin was added to the dialyzed solution for reaction at 37° C. for 2 hours to produce the streptavidin-labeled anti-Lp-PLA2 antibodies.

(3) Purification of the solution of streptavidin-labeled anti-Lp-PLA2 antibodies in the above reaction with a G-25 gel column.

(4) An equal volume of 5 g/ml BSA protective solution was added to the purified solution of streptavidin-labeled anti-Lp-PLA2 antibodies to obtain the final solution.

Preparation Example 8: Preparation of a Solution of Anti-Lp-PLA2 Monoclonal or Polyclonal Antibodies Labeled with Anti-FITC Monoclonal or Polyclonal Antibodies (1) Preparation of pH 9.5 dialysis solution: in a 5000 ml beaker, 14.31 g of $Na_2CO_3$ and 26.46 g of $NaHCO_3$ was added, and filled up to 4500 ml with water. The dialysate prepared was placed on a magnetic stirrer for later use.

(2) A dialysis bag with an interception capacity of 14000 was chosen, a portion of which with appropriate size was prepared for later use. 1 mg of anti-Lp-PLA2 monoclonal or polyclonal antibodies was dissolved and adjusted to 1 ml with the dialysis solution prepared above, and placed into the dialysis bag. Dialysis was performed under stirring for 2 hours, and 50 μg of anti-FITC monoclonal or polyclonal antibodies was added to the dialyzed solution for reaction at 37° C. for 2 hours to produce the solution of anti-Lp-PLA2 monoclonal or polyclonal antibodies labeled with anti-FITC monoclonal or polyclonal antibodies.

(3) Purification of the solution of anti-Lp-PLA2 monoclonal or polyclonal antibodies labeled with anti-FITC monoclonal or polyclonal antibodies obtained in the above reaction was performed on a G-25 gel column.

(4) An equal volume of 5 g/ml of BSA protective solution was added to the solution of anti-Lp-PLA2 monoclonal or polyclonal antibodies labeled with anti-FITC monoclonal or polyclonal antibodies to obtain the final solution.

Preparation Example 9: Preparation of a Biotinylated ABEI Solution (1) Preparation of pH 9.5 dialysis solution: in a 5000 ml beaker, 14.31 g of $Na_2CO_3$ and 26.46 g of $NaHCO_3$ was added, and filled up to 4500 ml with water. The dialysate prepared was placed on a magnetic stirrer for later use.

(2) A dialysis bag with an interception capacity of 14000 was chosen, a portion of which with prepared for later use. 1 mg of biotin was dissolved and adjusted to 1 ml with the dialysis solution prepared above, and placed into the dialysis bag. Dialysis was performed under stirring for 2 hours, and 300 µg of ABEI-hemisuccinimide-N-hydroxysuccinimide was added to the dialyzed solution for reaction at 37° C. for 2 hours to produce the solution of biotinylated ABEI solution.

(3) Purification of the biotinylated ABEI solution obtained in the above reaction was performed on a G-25 gel column.

(4) An equal volume of 5 g/ml BSA protective solution was added to the purified biotinylated ABEI solution to obtain the final solution.

In the following embodiments:

the first anti-Lp-PLA2 antibody was purchased from Diazyme Laboratories (USA), Catalog No. SDJ710044, Clone No. 2A7A3;

the second anti-Lp-PLA2 antibody was purchased from Diazyme Laboratories (USA), Catalog No. SDJ710041, Clone No. 3F1E1;

the goat anti-FITC polyclonal antibody was purchased from the Jackson Laboratory (USA);

the FITC was purchased from Shanghai Jining Shiye Co., Ltd.;

the Lp-PLA2 standards were purchased from Diazyme Laboratories (USA);

the ABEI was available from Shenzhen New Industries Biomedical Engineering Co., Ltd.;

the magnetic microspheres were manufactured by Shenzhen New Industries Biomedical Engineering Co., Ltd., with 80% particle size distribution of 1-5 µm, precipitation time of 10 to 15 seconds at a magnetic intensity of 4000 gauss, and protein adsorption concentration of 0.8 mg to 1.2 mg at 30 mg BSA;

the biotin and streptavidin were both purchased from Biosources (USA); and the Maglumi 2000 chemiluminescence analyzer was available from Shenzhen New Industries Biomedical Engineering Co., Ltd.

Example 1

The first anti-Lp-PLA2 antibodies were used to prepare a suspension of magnetic sphere coated with the first anti-Lp-PLA2 antibodies according to Preparation Example 1.

The second anti-Lp-PLA2 antibodies were used to prepare a suspension of the second anti-Lp-PLA2 antibodies labeled with ABEI according to Preparation Example 4.

Preparation of the displacer: To a beaker, 1000 ml of purified water was added, and 15 g of CHAPS, 0.5 g of casein, 2 g of EDTA-2Na, 6 g of DDT, 1 g of Tris, 3 g of MES, and 2 g of $NaN_3$ were weighed and dissolved in the water in sequence. After complete dissolution of the above, 150 ml of newborn bovine serum, 5 ml of acetic acid, 25 ml of horse serum, 10 ml of glycerol, and 25 g of BSA were added, well mixed, and then filtered to obtain the displacer solution.

Preparation of the calibrator dilution: 0.2 g of $KH_2PO_4$, 2.9 g of $Na_2HPO_4 \cdot 12H_2O$, 8 g of NaCl, 5 g of BSA, 2 g of $NaN_3$, and 0.125 g of $MgCl_2$ were accurately weighed with an analytical balance, to which purified water was slowly added to adjust the volume to 1000 ml, stirred to fully dissolve the solids, and filtered with a filter membrane with 0.45 µm pore size for later use.

Preparation of the high-point calibrator solution and low-point calibrator solution: An appropriate amount of Lp-PLA2 standard was taken and prepared into a high-point calibrator solution of 562.43 ng/ml and a low-point calibrator solution of 17.8 ng/ml using the dilution above.

The kit of the present example comprises each solution prepared as above.

Lp-PLA2 in a sample was detected using a Maglumi 2000 plus chemiluminescence immunoassay analyser with the following general procedure:

1) adding 20 µl of the subject sample or the calibrator to the cuvette;

2) adding 50 µl of the displacer, 50 µl of the second anti-Lp-PLA2 antibody solution labeled with ABEI, and 20 µl of the suspension of the magnetic sphere coated with the first anti-Lp-PLA2 antibodies, and incubating for 30 minutes at 37° C.;

3) cleaning by automatic perfusion of a system buffer;

4) adding a chemiluminescent substrate (manufactured by New Industries Biomedical Engineering Co., Ltd., catalog No.: 130299004M) and measuring the relative luminous intensity; and 5) calculate automatically the LP-PLA2 concentration of the sample using the luminous intensity of the sample by the working curve calibrated with the calibrator.

Determination of linearity: Lp-PLA2 standards were prepared into solutions of 0 ng/ml to 1000 ng/ml and the concentrations of the standards were linearly fit with the detected luminous intensities to verify the linearity of the ten-point calibration curve. The results are shown in Table 1 and shown in FIG. 1.

Determination of sensitivity: detection sensitivity was tested 20 times with the dilutions. The results are shown in Table 2.

Determination of precision: The high-point calibration was tested repeated for ten times to calculate the relative standard deviation (Cv). The results are shown in Table 3.

Determination of recovery: The doubling dilution of the high-point calibrator was measured for ten times, the average of which was then obtained to calculate the ratio of the average to the 50% theoretical concentration of the high-point calibrator. The results are shown in Table 4.

Example 2

Figure 2:
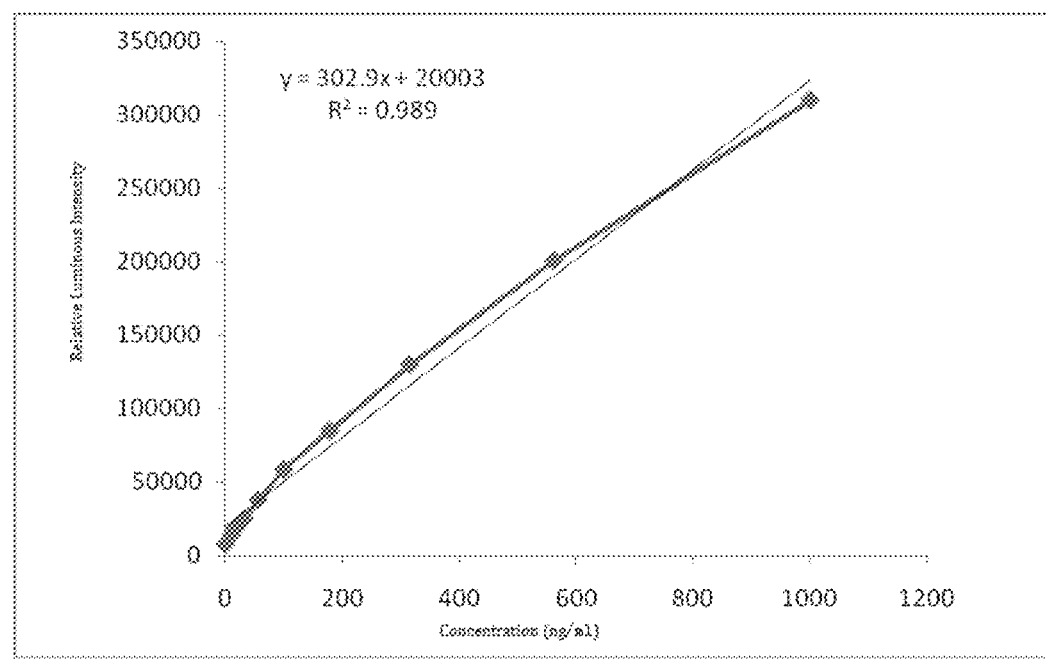
FIG. 2 shows a linear fit plot of the Lp-PLA2 concentration and the relative luminous intensity according to Example 2.

The kit composition and detection method of this embodiment were substantially the same as in Example 1, except that the present embodiment does not use a displacer. The results are shown in Table 1-4 and FIG. 2.

Example 3

A suspension of magnetic sphere coated with the goat anti-FITC polyclonal antibodies prepared as described in Preparation Example 3 above.

The first anti-Lp-PLA2 antibodies were used to prepare a solution of the first anti-Lp-PLA2 antibodies labeled with ABEI according to Preparation Example 4.

The second anti-Lp-PLA2 antibodies were used to prepare a solution of the second anti-Lp-PLA2 antibodies labeled with FITC according to Preparation Example 6.

Preparation of the displacer: To a beaker, 1000 ml of purified water was added, and 3 g of ANS, 1 g of casein, 3 g of EDTA-2Na, 6 g of DDT, 1 g of Tris, 3 g of MES, and 2 g of $NaN_3$ were weighed and dissolved in the water in sequence. After complete dissolution of the above, 200 ml of newborn bovine serum, 5 ml of acetic acid, 30 ml of horse serum, 10 ml of glycol, and 25 g of BSA were measured and added, well mixed, and then filtered to obtain the displacer.

A high-point calibrator solution of 562.43 ng/ml and a low-point calibrator solution of 17.8 ng/ml were prepared.

The kit of the present example comprises each solution prepared as above.

The detection procedure of Lp-PLA2 was substantially the same as that of Example 1, except for step 2): adding 40 μl of the displacer, 40 μl of the second anti-Lp-PLA2 antibody solution labeled with ABEI, 40 μl of the suspension of the magnetic sphere coated with the goat anti-FITC polyclonal antibodies, and 40 μl of the solution of the first anti-Lp-PLA2 antibodies labeled with FITC, and incubating for 30 minutes at 37° C.

Figure 3:
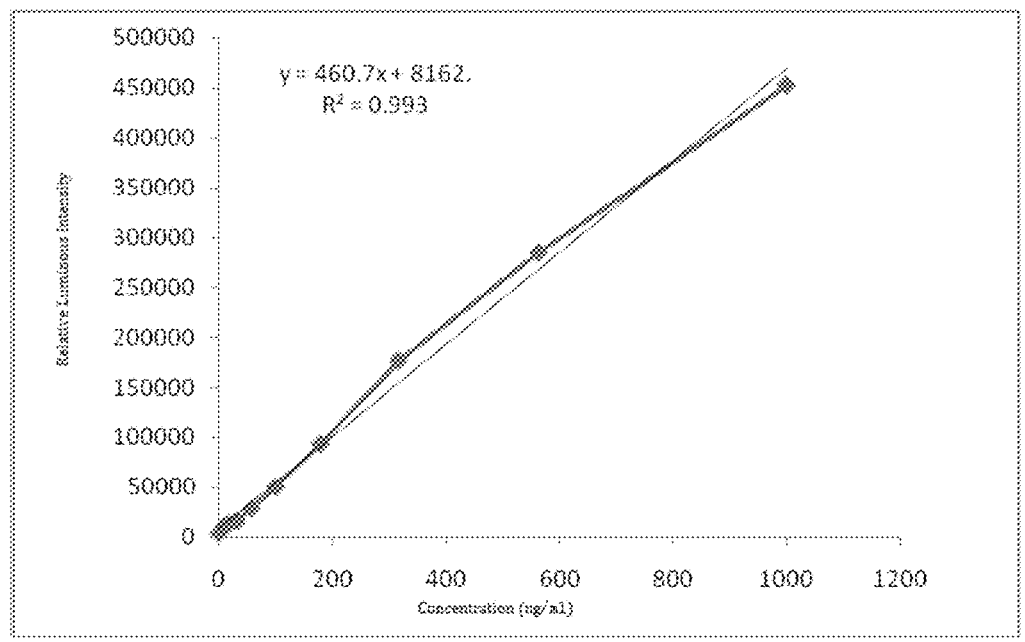
FIG. 3 shows a linear fit plot of the Lp-PLA2 concentration and the relative luminous intensity according to Example 3.

The results are shown in Table 1-4 and FIG. 3.

Example 4

Figure 4:
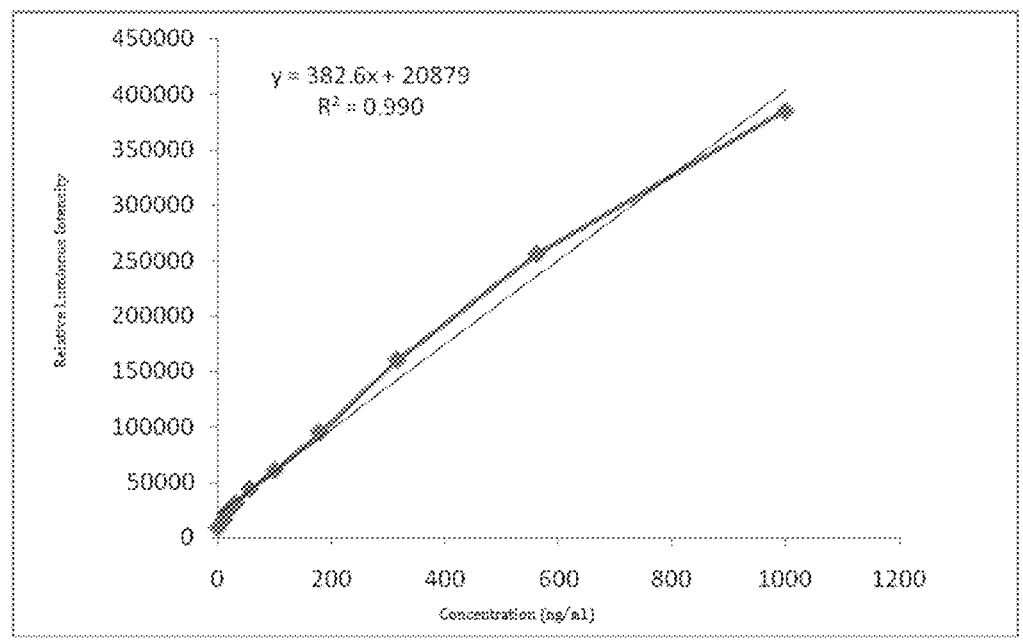
FIG. 4 shows a linear fit plot of the Lp-PLA2 concentration and the relative luminous intensity according to Example 4.

The kit composition and the detection method of this embodiment were substantially the same as those of Example 3, except that the displacer is not used in the present embodiment. The results are shown in Table 1-4 and FIG. 4.

Example 5

A suspension of magnetic sphere coated with streptavitin was prepared as described in Preparation Example 2 above.

The first anti-Lp-PLA2 antibodies were used to prepare a solution of the first anti-Lp-PLA2 antibodies labeled with biotin according to Preparation Example 5.

The second anti-Lp-PLA2 antibodies were used to prepare a solution of the second anti-Lp-PLA2 antibodies labeled with ABEI according to Preparation Example 4.

Preparation of the displacer: To a beaker, 1000 ml of purified water was added, and 5 g of sodium deoxycholate, 2 g of casein, 2 g of EDTA-2Na, 5 g of DDT, 1.5 g of Tris, 2 g of MES, and 2 g of $NaN_3$ were weighed and dissolved in the water in sequence. After complete dissolution of the above, 100 ml of newborn bovine serum, 8 ml of acetic acid, 20 ml of goat serum, 5 ml of glycol, and 25 g of BSA were measured and added, well mixed, and then filtered to obtain the displacer.

A high-point calibrator solution of 562.43 ng/ml and a low-point calibrator solution of 17.8 ng/ml were prepared.

The kit of the present example comprises each solution prepared as above.

The detection procedure of Lp-PLA2 was substantially the same as that of Example 1, except for step 2): adding 50 μl of the displacer, 50 μl of the second anti-Lp-PLA2 antibody solution labeled with ABEI, 20 μl of the magnetic sphere coated with streptavitin, and 20 μl of the solution of the first anti-Lp-PLA2 antibodies labeled with biotin, and incubating for 30 minutes at 37° C.

Figure 5:
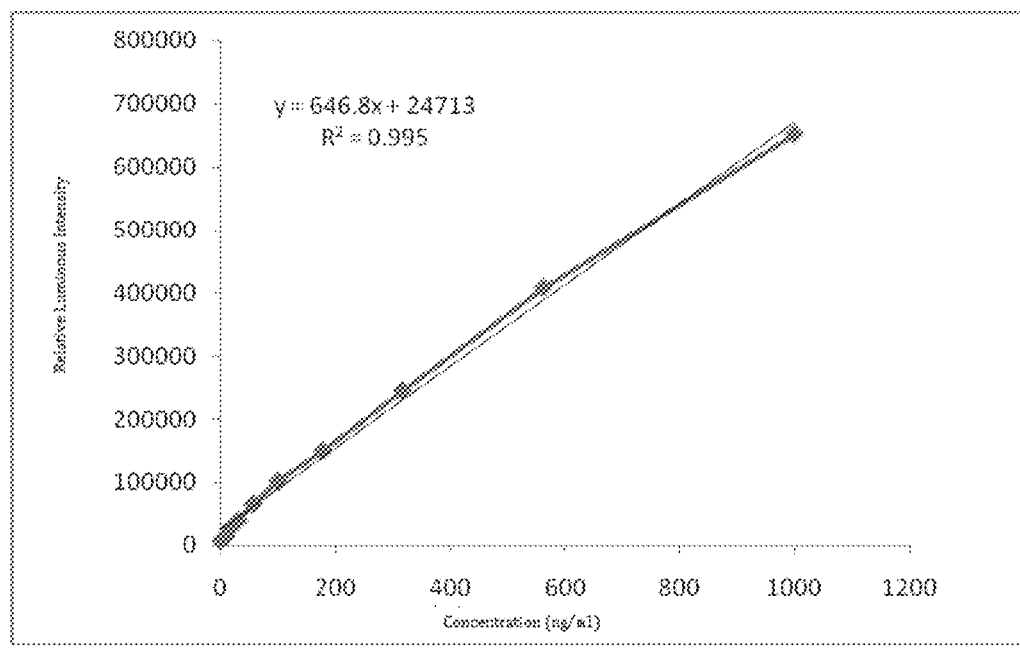

The results are shown in Table 1-4 and FIG. 5.

Example 6

Figure 6:
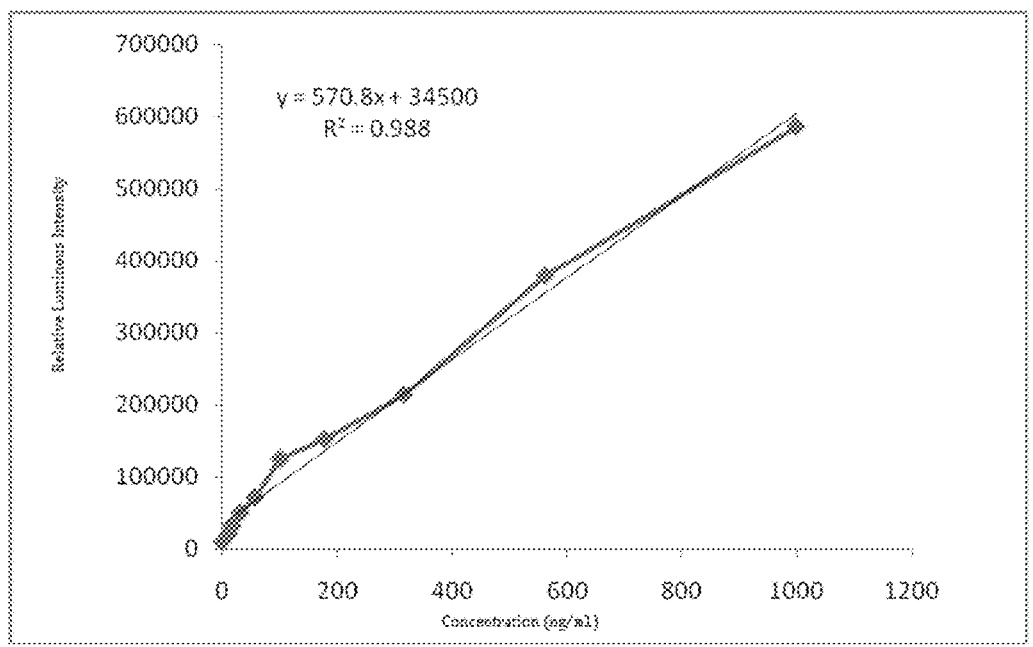

The kit composition and the detection method of this kit were substantially the same as those of Example 5, except that the displacer is not used in the present embodiment. The results are shown in Table 1-4, FIG. 6.

Example 7

The Lp-PLA2 concentrations of ten negative samples and ten positive samples were measured using each of the kits in Examples 1 to 6 described above, respectively, and the samples were each measured twice. The results are shown in Table 5.

TABLE 1

| Relative Luminous Intensity | Concentration (ng/ml) | | | | | | | | |
|---|---|---|---|---|---|---|---|---|---|
| | 0 | 10 | 17.8 | 31.56 | 56.28 | 100 | 177.9 | 316.33 | 562.43 | 1000 |
| Example 1 | 2524 | 8245 | 11940 | 18773 | 32099 | 53212 | 84913 | 140003 | 241083 | 400057 |
| Example 2 | 7854 | 14245 | 18945 | 24754 | 38054 | 58645 | 84916 | 130003 | 201083 | 310027 |
| Example 3 | 3562 | 10845 | 13034 | 15608 | 28254 | 49895 | 93560 | 176845 | 284587 | 452378 |
| Example 4 | 8512 | 15689 | 23018 | 30214 | 44125 | 60214 | 94587 | 160254 | 256112 | 385461 |
| Example 5 | 8457 | 15241 | 27845 | 40125 | 66542 | 102315 | 150124 | 245781 | 408281 | 652314 |
| Example 6 | 10201 | 20147 | 32157 | 50568 | 72314 | 124784 | 152245 | 214512 | 378841 | 586451 |

TABLE 2

| | Example 1 | | Example 2 | | Example 3 | | Example 4 | | Example 5 | | Example 6 | |
|---|---|---|---|---|---|---|---|---|---|---|---|---|
| ID# | Luminous | Concentration* | Luminous | Concentration | Luminous | Concentration | Luminous | Concentration | Luminous | Concentration | Luminous | Concentration |
| A1 | 2463 | 0 | 7865 | 0.94 | 3518 | 0 | 8534 | 0.85 | 8563 | 0 | 10195 | 1.97 |
| A2 | 2504 | 0 | 7726 | 0.84 | 3464 | 0 | 8592 | 0.51 | 8328 | 0 | 9941 | 1.96 |
| A3 | 2490 | 0 | 7743 | 0.72 | 3416 | 0 | 8413 | 0.85 | 8702 | 0 | 9829 | 1.91 |
| A4 | 2447 | 0 | 7877 | 0.99 | 3352 | 0 | 8558 | 0.77 | 8722 | 0 | 10306 | 2.00 |
| A5 | 2457 | 0 | 7811 | 0.99 | 3510 | 0 | 8467 | 0.92 | 8548 | 0 | 9606 | 1.77 |
| A6 | 2507 | 0 | 7746 | 1.00 | 3578 | 0 | 8516 | 0.62 | 8425 | 0 | 10070 | 1.70 |
| A7 | 2551 | 0 | 7763 | 0.79 | 3528 | 0 | 8474 | 0.86 | 8698 | 0 | 10188 | 1.99 |
| A8 | 2486 | 0 | 7837 | 0.80 | 3579 | 0 | 8550 | 0.89 | 8358 | 0 | 10362 | 1.36 |
| A9 | 2528 | 0 | 7818 | 0.76 | 3438 | 0 | 8608 | 0.67 | 8635 | 0 | 9757 | 1.50 |
| A10 | 2445 | 0 | 7818 | 0.73 | 3471 | 0 | 8552 | 0.85 | 8270 | 0 | 9940 | 1.65 |
| A11 | 2486 | 0 | 7828 | 1.00 | 3564 | 0 | 8521 | 0.82 | 8450 | 0 | 10042 | 1.76 |
| A12 | 2470 | 0 | 7790 | 1.18 | 3651 | 0 | 8474 | 0.59 | 8731 | 0 | 9987 | 1.91 |
| A13 | 2469 | 0 | 7787 | 0.90 | 3424 | 0 | 8405 | 0.83 | 8285 | 0 | 9856 | 1.88 |
| A14 | 2545 | 0 | 7834 | 0.90 | 3561 | 0 | 8469 | 0.59 | 8816 | 0 | 9982 | 1.49 |
| A15 | 2492 | 0 | 7797 | 0.84 | 3405 | 0 | 8576 | 0.84 | 8598 | 0 | 9859 | 1.82 |
| A16 | 2482 | 0 | 7811 | 0.76 | 3319 | 0 | 8710 | 0.53 | 8325 | 0 | 9964 | 1.77 |

TABLE 2-continued

| ID# | Example 1 | | Example 2 | | Example 3 | | Example 4 | | Example 5 | | Example 6 | |
|---|---|---|---|---|---|---|---|---|---|---|---|---|
| | Luminous | Concentration* | Luminous | Concentration | Luminous | Concentration | Luminous | Concentration | Luminous | Concentration | Luminous | Concentration |
| A17 | 2445 | 0 | 7760 | 1.01 | 3714 | 0 | 8578 | 0.58 | 8721 | 0 | 10173 | 1.72 |
| A18 | 2565 | 0 | 7744 | 1.09 | 3395 | 0 | 8506 | 0.76 | 8244 | 0 | 9652 | 1.80 |
| A19 | 2491 | 0 | 7818 | 1.15 | 3484 | 0 | 8400 | 0.88 | 8214 | 0 | 9944 | 1.40 |
| A20 | 2450 | 0 | 7774 | 1.00 | 3567 | 0 | 8589 | 0.76 | 8517 | 0 | 9802 | 1.71 |

*Concentration in ng/ml.

TABLE 3

| Determined Concentration* | ID# | | | | | | | | | | Cv (%) |
|---|---|---|---|---|---|---|---|---|---|---|---|
| | 1 | 2 | 3 | 4 | 5 | 6 | 7 | 8 | 9 | 10 | |
| Example 1 | 551.32 | 568.47 | 555.14 | 563.57 | 559.37 | 563.58 | 566.47 | 557.34 | 558.36 | 556.99 | 1.52 |
| Example 2 | 520.78 | 552.32 | 546.91 | 530.54 | 520.12 | 579.35 | 570.15 | 566.70 | 574.55 | 582.10 | 4.31 |
| Example 3 | 563.55 | 556.65 | 559.51 | 565.74 | 553.12 | 566.54 | 555.48 | 568.25 | 557.40 | 569.28 | 1.04 |
| Example 4 | 598.55 | 522.41 | 570.99 | 598.48 | 543.84 | 570.72 | 557.41 | 572.77 | 546.03 | 559.78 | 4.21 |
| Example 5 | 578.30 | 556.64 | 560.67 | 559.42 | 546.84 | 561.50 | 573.50 | 557.47 | 572.08 | 577.98 | 1.85 |
| Example 6 | 596.22 | 546.58 | 539.86 | 545.80 | 541.29 | 532.55 | 567.03 | 537.72 | 586.53 | 541.57 | 3.98 |

*Concentration in ng/ml.

TABLE 4

| ID# | Determined Concentration* | | | | | |
|---|---|---|---|---|---|---|
| | Example 1 | Example 2 | Example 3 | Example 4 | Example 5 | Example 6 |
| 1 | 274.99 | 269.77 | 267.08 | 255.54 | 272.50 | 273.41 |
| 2 | 273.24 | 279.69 | 270.56 | 256.39 | 292.45 | 269.74 |
| 3 | 275.12 | 275.19 | 271.38 | 241.62 | 268.56 | 260.58 |
| 4 | 280.16 | 268.37 | 271.49 | 240.67 | 293.61 | 249.71 |
| 5 | 280.28 | 274.64 | 264.76 | 276.02 | 277.48 | 274.32 |
| 6 | 282.42 | 272.90 | 262.60 | 249.01 | 282.94 | 255.85 |
| 7 | 276.07 | 262.92 | 265.39 | 250.16 | 283.43 | 246.13 |
| 8 | 277.11 | 263.97 | 274.98 | 271.03 | 278.83 | 246.59 |
| 9 | 281.24 | 267.53 | 270.64 | 239.18 | 277.79 | 251.41 |
| 10 | 279.89 | 254.72 | 273.48 | 266.37 | 275.91 | 271.08 |
| Average | 278.05 | 268.97 | 269.24 | 254.60 | 280.35 | 259.88 |
| Theoretical Value | 281.22 | 281.22 | 281.22 | 281.22 | 281.22 | 281.22 |
| % Recovery | 98.9% | 95.6% | 95.7% | 90.5% | 99.7% | 92.4% |

*Concentration in ng/ml.

TABLE 5

| Subject Sample | | Example 1 Kit: Determined Concentration (ng/ml) | Example 2 Kit: Determined Concentration (ng/ml) | Example 3 Kit: Determined Concentration (ng/ml) | Example 4 Kit: Determined Concentration (ng/ml) | Example 5 Kit: Determined Concentration (ng/ml) | Example 6 Kit: Determined Concentration (ng/ml) |
|---|---|---|---|---|---|---|---|
| Negative Sample | 1 | 0.110 | 0.285 | 0.147 | 0.558 | 0.105 | 0.698 |
| | | 0.102 | 0.369 | 0.138 | 0.79 | 0.114 | 0.553 |
| | 2 | 0.501 | 0.705 | 0.523 | 0.668 | 0.514 | 0.518 |
| | | 0.511 | 0.532 | 0.512 | 0.458 | 0.51 | 0.663 |
| | 3 | 2.551 | 2.489 | 2.513 | 2.658 | 2.54 | 2.754 |
| | | 2.548 | 2.596 | 2.532 | 2.447 | 2.524 | 2.574 |
| | 4 | 35.214 | 35.896 | 34.698 | 35.467 | 35.012 | 35.004 |
| | | 35.665 | 35.025 | 35.689 | 35.447 | 35.896 | 35.689 |
| | 5 | 5.667 | 5.489 | 5.632 | 5.996 | 5.638 | 4.998 |
| | | 5.602 | 5.705 | 5.601 | 4.689 | 5.665 | 5.235 |
| | 6 | 121.321 | 120.698 | 120.369 | 121.587 | 120.358 | 122.587 |
| | | 120.985 | 119.687 | 120.546 | 121.458 | 120.365 | 120.698 |
| | 7 | 98.567 | 98.269 | 98.447 | 99.325 | 98.963 | 98.559 |
| | | 98.663 | 97.895 | 98.542 | 97.896 | 98.125 | 98.657 |
| | 8 | 153.265 | 152.685 | 153.021 | 153.963 | 153.264 | 154.689 |
| | | 153.986 | 153.558 | 153.214 | 152.578 | 153.001 | 152.036 |
| | 9 | 101.254 | 99.689 | 100.256 | 104.257 | 101.254 | 102.345 |
| | | 100.568 | 101.258 | 102.302 | 100.256 | 102.356 | 101.559 |

TABLE 5-continued

| Subject Sample | | Example 1 Kit: Determined Concentration (ng/ml) | Example 2 Kit: Determined Concentration (ng/ml) | Example 3 Kit: Determined Concentration (ng/ml) | Example 4 Kit: Determined Concentration (ng/ml) | Example 5 Kit: Determined Concentration (ng/ml) | Example 6 Kit: Determined Concentration (ng/ml) |
|---|---|---|---|---|---|---|---|
| | 10 | 18.256 | 18.965 | 18.457 | 18.569 | 18.003 | 19.568 |
| | | 18.001 | 17.458 | 18.012 | 18.023 | 19.045 | 17.896 |
| Positive Sample | 11 | 293.847 | 290.368 | 295.874 | 300.256 | 296.358 | 298.562 |
| | | 294.990 | 296.385 | 293.589 | 292.354 | 295.257 | 292.547 |
| | 12 | 356.258 | 361.025 | 358.264 | 359.245 | 356.845 | 352.236 |
| | | 350.286 | 354.258 | 356.325 | 353.478 | 355.889 | 358.687 |
| | 13 | 887.568 | 899.647 | 895.578 | 887.569 | 896.385 | 896.357 |
| | | 895.678 | 879.658 | 893.578 | 895.124 | 895.265 | 889.568 |
| | 14 | 754.623 | 765.235 | 756.326 | 762.356 | 758.265 | 762.148 |
| | | 756.235 | 758.231 | 758.154 | 755.256 | 754.264 | 754.995 |
| | 15 | 524.562 | 526.985 | 522.398 | 522.689 | 524.687 | 530.687 |
| | | 522.324 | 518.569 | 528.658 | 532.014 | 523.214 | 533.201 |
| | 16 | 469.521 | 468.231 | 466.302 | 465.896 | 466.325 | 469.302 |
| | | 466.278 | 460.259 | 460.256 | 462.389 | 466.589 | 458.589 |
| | 17 | 359.865 | 350.269 | 358.265 | 356.369 | 359.564 | 361.254 |
| | | 358.663 | 362.015 | 355.026 | 351.485 | 354.789 | 352.647 |
| | 18 | 289.458 | 280.265 | 285.689 | 290.258 | 288.562 | 292.356 |
| | | 287.245 | 287.569 | 286.33 | 281.667 | 286.598 | 282.113 |
| | 19 | 668.569 | 666.325 | 668.668 | 654.239 | 675.125 | 678.593 |
| | | 666.201 | 671.254 | 668.015 | 663.596 | 670.215 | 660.368 |
| | 20 | 986.258 | 978.568 | 985.236 | 987.259 | 988.124 | 986.359 |
| | | 988.235 | 982.135 | 988.478 | 980.236 | 982.359 | 993.331 |

As can be seen from Table 1 and FIGS. 1 to 6, the kit provided herein has a fitted linear correlation coefficient of greater than 0.98 for the ten-point curve obtained from ten different concentrations of the standard solution, indicating that the kit provided herein can linearly reflect the Lp-PLA2 concentration in the human body with luminous intensity. The kits of Examples 2, 4, and 6 that did not comprise a displacer showed a ten-point curve with a linear correlation coefficient of about 0.99. Examples 1, 3 and 5 that comprised the displacer provided herein showed a linear correlation coefficient greater than 0.99, which was greater than the corresponding kits without the displacer, indicating that the displacer was able to improve the linear correlation of the Lp-PLA2concentration reflected by the luminous intensity of the kit.

As can be seen from Table 2, in spite of the different composition of kits in Examples 1, 3, and 5, the concentration of Lp-PLA2 in the sample dilutions were all detected as 0, indicating that the kits had high sensitivity and strong resistance to interference. The kits of Examples 2, 4, and 6 that did not comprise a displacer had detected Lp-PLA2 concentrations greater than zero in sample dilutions, indicating that addition of the displacer to the kit provided herein could significantly improve the detection accuracy and sensitivity.

The data in Table 3 show that the results of the concentration determination of the high-point calibrator measured with the kits of Examples 1 to 6 had CVs lower than 5%. In particular, the CVs of Examples 1, 3, and 5 were lower than 2%, indicating good repeatability of the kits. Compared with the kits of Examples 2, 4, and 6, it also showed that the displacer was able to improve the repeatability of the kit.

As can be seen from the data in Table 4, the 50% concentration of the high-point calibrator measured in Examples 1 to 6 did not deviated much from the theoretical values, i.e., the 50% theoretical concentration of the high-point calibrator. The recovery percentage ranged between 90% and 110%. However, the recovery percentages of the kits of Examples 1, 3, and 5 that comprised the displacer were higher than those kits without the displacer, indicating that the displacer provided herein were able to improve the determined recovery of the kits.

As can be seen from the data in Table 5, when the Lp-PLA2 concentration of the sample was close to the minimum detection limit, the kit comprising the displacer (the kits of Examples 1, 3 and 5) was capable of sensitive detection of the sample value. This indicates that the kits comprising the displacer were more sensitive than those without. Meanwhile, comparing the the sample test results of the different kits, it can be found that the kits comprising the displacer had better repeatability of the determination results than those without.

The results of the above embodiments show that all parameters determined were highly compliant with the quality standards, especially the kits containing the displacer, indicating that the kit design is reasonable to meet the requirements for detection of Lp-PLA2.

Furthermore, according to the Lp-PLA2 detection method provided herein, detection of a sample can be completed in 40 minutes, which greatly improves the detection efficiency at least by double compared with the conventional chemiluminescence enzyme-linked immunosorbent assay.

While the disclosure has been described in detail, modifications within the spirit and scope of the disclosure will be apparent to those skilled in the art. In addition, it should be understood that various aspects of the disclosure, various parts of the various embodiments, and various features recited may be combined or interchangeable in full or in part. In each of the specific embodiments above, those embodiments which refer to another embodiment may be suitably combined with other embodiments, as will be understood by those skilled in the art. Furthermore, it will be understood by those skilled in the art that the foregoing description is only for the purpose of illustration by way of example and is not intended to limit the disclosure.

The invention claimed is:

1. A kit for detecting lipoprotein-associated phospholipase A2, comprising one or more first anti-lipoprotein-associated phospholipase A2 antibodies coated on a magnetic sphere for binding with lipoprotein-associated phospholipase A2 to be detected, and one or more second anti-lipoprotein-associated phospholipase A2 antibodies labeled with a trace marker for binding with the lipoprotein-associated phospholipase A2 to be detected at other binding sites different from the binding sites of the first anti-lipoprotein-associated phospholipase A2 antibodies with the lipoprotein-associated phospholipase A2 to be detected;
    wherein the trace marker is at least one selected from the group consisting of luminol and derivatives thereof, isoluminol and derivatives thereof, and acridinium esters; and
    wherein the kit further comprises a displacer including water as a solvent and the following components:
        at least one selected from the group consisting of 3-[3-(cholamidopropyl) dimethylammonio] propanesulfonate, 8-anilino-1-naphthalenesulfonic acid, sodium deoxycholate, barbiturate, and acetic acid;
        newborn bovine serum;
        goat serum and/or horse serum;
        dithiothreitol;
        tris (hydroxymethyl) aminomethane;
        hydrated 2-morpholinoethanesulfonic acid;
        casein; and
        disodium ethylenediaminetetraacetate.

2. The kit according to claim 1, wherein the first anti-lipoprotein-associated phospholipase A2 antibodies and the second anti-lipoprotein-associated phospholipase A2 antibodies are independently anti-lipoprotein-associated phospholipase A2 monoclonal antibodies and/or anti-lipoprotein-associated phospholipase A2 polyclonal antibodies.

3. The kit according to claim 2, wherein the trace marker is N-(4-aminobutyl)-N-ethylisoluminol.

4. The kit according to claim 2, wherein the magnetic sphere is a complex of $Fe_2O_3$ or $Fe_3O_4$ magnetic particles and an organic polymeric material and has a particle size of 0.1 to 5 microns; and, the magnetic sphere are optionally modified by surface modification to carry one or more active functional groups.

5. The kit according to claim 2, wherein the first anti-lipoprotein-associated phospholipase A2 antibodies are directly or indirectly coated on the magnetic sphere, and the indirect coating forms include indirect coating via a fluorescein isothiocyanate and anti-fluorescein isothiocyanate antibody system or a streptavidin and biotin system; and
    the trace marker directly or indirectly labels the second anti-lipoprotein-associated phospholipase A2 antibodies and the indirect labeling forms include indirect labeling via a fluorescein isothiocyanate and anti-fluorescein isothiocyanate antibody system or a streptavidin and biotin system.

6. The kit according to claim 1, wherein the kit comprises the following components in an amount relative to the total amount of the solvent:
    at least one selected from the group consisting of 0.1 to 5 wt % of 3-[3-(cholamidopropyl) dimethylammonio] propanesulfonate, 0.1 to 2 wt % of 8-anilino-1-naphthalenesulfonic acid, 0.1 to 2 wt % of sodium deoxycholate, 0.1 to 2 wt % of barbiturate, and 0.1 to 2 vol % of acetic acid;
    1 to 50 vol % of newborn bovine serum;
    0.1 to 10 vol % of goat serum and/or 0.1 to 10 vol % of horse serum;
    0.1 to 10 wt % of dithiothreitol;
    0.1 to 10 wt % of tris (hydroxymethyl) aminomethane;
    0.1 to 10 wt % of monohydrate 2-morpholinoethanesulfonic acid;
    0.01 to 1 wt % of casein; and
    0.01 to 1 wt % of disodium ethylenediaminetetraacetate.

7. The kit of claim 6, wherein the kit further comprises a low-point calibrator and a high-point calibrator of lipoprotein-associated phospholipase A2 and optionally a buffer.

8. The kit according to claim 2, wherein the concentrations of the first anti-lipoprotein-associated phospholipase A2 antibodies and the second anti-lipoprotein-associated phospholipase A2 antibodies in the kit are each 10 to 200 µg/ml, the concentration of the trace marker is 0.1 to 1 mg/ml, and the concentration of the magnetic sphere is 0.1 to 5 mg/ml.

9. A method for preparing a kit for detecting lipoprotein-associated phospholipase A2, comprising:
    directly or indirectly coating a first anti-lipoprotein-associated phospholipase A2 antibody on magnetic sphere, and directly or indirectly labeling a second anti-lipoprotein-associated phospholipase A2 antibody with a trace marker, to obtain the kit including one or more first anti-lipoprotein-associated phospholipase A2 antibodies coated on magnetic sphere for binding with lipoprotein-associated phospholipase A2 to be detected, and one or more second anti-lipoprotein-associated phospholipase A2 antibodies labeled with a trace marker for binding with lipoprotein-associated phospholipase A2 to be detected at other binding sites different from the binding sites of the first anti-Lipoprotein-associated phospholipase A2 antibodies with lipoprotein-associated phospholipase A2 to be detected;
    wherein the trace marker is at least one selected from the group consisting of luminol and its derivatives, isoluminol and its derivatives, and acridinium esters; and
    wherein the method further comprises a step of preparing a displacer as a component of the kit, including: mixing water as a solvent and the following components:
    at least one selected from the group consisting of 3-[3-(cholamidopropyl) dimethylammonio] propanesulfonate, 8-anilino-1-naphthalenesulfonic acid, sodium deoxycholate, barbiturate, and acetic acid;
    newborn bovine serum;
    goat serum and/or horse serum;
    dithiothreitol;
    tris (hydroxymethyl) aminomethane;
    hydrated 2-morpholinoethanesulfonic acid;
    casein; and
    disodium ethylenediaminetetraacetate.

10. The method according to claim 9, wherein
    the indirect coating includes coating the first anti-lipoprotein-associated phospholipase A2 antibody indirectly via a fluorescein isothiocyanate and anti-fluorescein isothiocyanate antibody system or a streptavidin and biotin system; and
    the indirect labeling includes labeling the second anti-lipoprotein-associated phospholipase A2 antibody via a fluorescein isothiocyanate and anti-fluorescein isothiocyanate antibody system or a streptavidin and biotin system.

11. A process according to claim 9, wherein the displacer comprises the following components in an amount relative to the total amount of the solvent:
    at least one selected from the group consisting of 0.1 to 5 wt % of 3-[3-(cholamidopropyl) dimethylammonio] propanesulfonate, 0.1 to 2 wt % of 8-anilino-1-naphthalenesulfonic acid, 0.1 to 2 wt % of sodium deoxycholate, 0.1 to 2 wt % of barbiturate, and 0.1 to 2 vol % of acetic acid;
    1 to 50 vol % of newborn bovine serum;
    0.1 to 10 vol % of goat serum and/or 0.1 to 10 vol % of horse serum;
    0.1 to 10 wt % of dithiothreitol;

0.1 to 10 wt % of tris (hydroxymethyl) aminomethane;
0.1 to 10 wt % of monohydrate 2-morpholinoethanesulfonic acid;
0.01 to 1 wt % of casein; and
0.01 to 1 wt % of disodium ethylenediaminetetraacetate.

12. The method according to claim 9, wherein the trace marker is N-(4-aminobutyl)-N-ethylisoluminol.

13. The method according to claim 9, wherein the magnetic sphere is a complex of $Fe_2O_3$ or $Fe_3O_4$ magnetic particles and an organic polymeric material and has a particle size of 0.1 to 5 microns.

14. The method according to claim 9, wherein, in the kit prepared, the concentrations of the first anti-lipoprotein-associated phospholipase A2 antibodies and the second anti-lipoprotein-associated phospholipase A2 antibodies are each 10 to 200 μg/ml, the concentration of the trace marker is 0.1 to 1 mg/ml, and the concentration of the magnetic sphere is 0.1 to 5 mg/ml.

15. A method for detecting lipoprotein-associated phospholipase A2, wherein the method comprises using a kit for detecting lipoprotein-associated phospholipase A2 to detect a concentration of lipoprotein-associated phospholipase A2 in a subject sample by chemiluminescence immunoassay, wherein the kit includes one or more first anti-lipoprotein-associated phospholipase A2 antibodies coated on magnetic sphere for binding with lipoprotein-associated phospholipase A2 to be detected, and one or more second anti-lipoprotein-associated phospholipase A2 antibodies labeled with a trace marker for binding with lipoprotein-associated phospholipase A2 to be detected at other binding sites different from the binding sites of the first anti-Lipoprotein-associated phospholipase A2 antibodies with lipoprotein-associated phospholipase A2 to be detected;
wherein the kit further comprises a displacer including water as a solvent and the following components:
at least one selected from the group consisting of 3-[3-(cholamidopropyl) dimethylammonio] propanesulfonate, 8-anilino-1-naphthalenesulfonic acid, sodium deoxycholate, barbiturate, and acetic acid;
newborn bovine serum;
goat serum and/or horse serum;
dithiothreitol;
tris (hydroxymethyl) aminomethane;
hydrated 2-morpholinoethanesulfonic acid;
casein; and
disodium ethylenediaminetetraacetate.

16. The method according to claim 15, wherein the trace marker is N-(4-aminobutyl)-N-ethylisoluminol.

17. The method according to claim 15, wherein the magnetic sphere is a complex of $Fe_2O_3$ or $Fe_3O_4$ magnetic particles and an organic polymeric material and has a particle size of 0.1 to 5 microns.

18. The method according to claim 15, wherein the first anti-lipoprotein-associated phospholipase A2 antibody is directly or indirectly coated on the magnetic sphere, and the indirect coating forms include coating the first anti-lipoprotein-associated phospholipase A2 antibody indirectly via a fluorescein isothiocyanate and anti-fluorescein isothiocyanate antibody system or a streptavidin and biotin system; and
the trace marker directly or indirectly labels the second anti-lipoprotein-associated phospholipase A2 antibody, and the indirect labeling forms include labeling the second anti-lipoprotein-associated phospholipase A2 antibody via a fluorescein isothiocyanate and anti-fluorescein isothiocyanate antibody system or a streptavidin and biotin system.

19. The method according to claim 15, wherein the kit comprises the following components in an amount relative to the total amount of the solvent:
at least one selected from the group consisting of 0.1 to 5 wt % of 3-[3-(cholamidopropyl) dimethylammonio] propanesulfonate, 0.1 to 2 wt % of 8-anilino-1-naphthalenesulfonic acid, 0.1 to 2 wt % of sodium deoxycholate, 0.1 to 2 wt % of barbiturate, and 0.1 to 2 vol % of acetic acid;
1 to 50 vol % of newborn bovine serum;
0.1 to 10 vol % of goat serum and/or 0.1 to 10 vol % of horse serum;
0.1 to 10 wt % of dithiothreitol;
0.1 to 10 wt % of tris (hydroxymethyl) aminomethane;
0.1 to 10 wt % of monohydrate 2-morpholinoethanesulfonic acid;
0.01 to 1 wt % of casein; and
0.01 to 1 wt % of disodium ethylenediaminetetraacetate.

20. The method according to claim 15, wherein, in the kit, the concentration of the first anti-lipoprotein-associated phospholipase A2 antibodies and the second anti-lipoprotein-associated phospholipase A2 antibodies are each 10 to 200 μg/ml, the concentration of the trace marker is 0.1 to 1 mg/ml, and the concentration of the magnetic sphere is 0.1 to 5 mg/ml.

* * * * *